United States Patent
Peng

(10) Patent No.: US 11,263,497 B2
(45) Date of Patent: Mar. 1, 2022

(54) METHOD AND SYSTEM FOR MACHINE LEARNING CLASSIFICATION BASED ON STRUCTURE OR MATERIAL SEGMENTATION IN AN IMAGE

(71) Applicant: StraxCorp Pty. Ltd., Melbourne (AU)

(72) Inventor: Yu Peng, Melbourne (AU)

(73) Assignee: STRAXCORP PTY. LTD., Victoria (AU)

( * ) Notice: Subject to any disclaimer, the term of this patent is extended or adjusted under 35 U.S.C. 154(b) by 47 days.

(21) Appl. No.: 16/448,474

(22) Filed: Jun. 21, 2019

(65) Prior Publication Data

US 2020/0401843 A1 Dec. 24, 2020

(51) Int. Cl.
*G06K 9/62* (2006.01)
*G06T 7/11* (2017.01)
(Continued)

(52) U.S. Cl.
CPC ............ *G06K 9/628* (2013.01); *A61B 5/4509* (2013.01); *A61B 5/4842* (2013.01);
(Continued)

(58) Field of Classification Search
CPC .... G06K 9/628; G06K 9/6257; G06K 9/6262; G06K 9/6269; G06K 9/6282; G06K 2209/05; G06T 7/11; G06T 7/0012; G06T 2207/20076; G06T 2207/20081; G06T 2207/20084; G06T 2207/30008; A61B 5/4509; A61B 5/4842; A61B 5/7267; A61B 5/7275
See application file for complete search history.

(56) References Cited

U.S. PATENT DOCUMENTS

2009/0028403 A1 1/2009 Bar-Aviv et al.
2013/0208970 A1 8/2013 Fujisawa
(Continued)

FOREIGN PATENT DOCUMENTS

WO WO-2010/115885 10/2010
WO WO-2019/106061 A1 6/2019

OTHER PUBLICATIONS

Australian Examination Report for Application No. 2019204380, dated Aug. 12, 2019.
(Continued)

*Primary Examiner* — Brenda C Bernardi
(74) *Attorney, Agent, or Firm* — Nixon Peabody LLP; Jeffrey L Costellia

(57) ABSTRACT

A system and method for classifying a structure or material in an image of a subject. The system comprises: a segmenter configured to form one or more segmentations of a structure or material in an image and generate from the segmentations one or more segmentation maps of the image including categorizations of pixels or voxels of the segmentation maps assigned from one or more respective predefined sets of categories; a classifier that implements a classification machine learning model configured to generate, based on the segmentations maps, one or more classifications and to assign to the classifications respective scores indicative of a likelihood that the structure or material, or the subject, falls into the respective classifications; and an output for outputting a result indicative of the classifications and scores.

16 Claims, 5 Drawing Sheets

(51) Int. Cl.
*A61B 5/00* (2006.01)
*G06T 7/00* (2017.01)

(52) U.S. Cl.
CPC .......... *A61B 5/7267* (2013.01); *A61B 5/7275* (2013.01); *G06K 9/6257* (2013.01); *G06K 9/6262* (2013.01); *G06T 7/0012* (2013.01); *G06T 7/11* (2017.01); *G06K 9/6269* (2013.01); *G06K 9/6282* (2013.01); *G06K 2209/05* (2013.01); *G06T 2207/20076* (2013.01); *G06T 2207/20081* (2013.01); *G06T 2207/20084* (2013.01); *G06T 2207/30008* (2013.01); *G06T 2207/30096* (2013.01)

(56) References Cited

U.S. PATENT DOCUMENTS

| | | | | |
|---|---|---|---|---|
| 2016/0171682 | A1* | 6/2016 | Abedini | G06T 7/0012 |
| | | | | 382/132 |
| 2017/0213339 | A1* | 7/2017 | Hibbard | G06K 9/6267 |
| 2018/0089505 | A1 | 3/2018 | El-Khamy et al. | |
| 2018/0315188 | A1 | 11/2018 | Tegzes et al. | |
| 2019/0005684 | A1* | 1/2019 | De Fauw | G06K 9/6292 |
| 2019/0065907 | A1 | 2/2019 | Strong et al. | |
| 2020/0410677 | A1* | 12/2020 | Keshwani | A61B 6/03 |
| 2021/0150714 | A1* | 5/2021 | Buerger | G06K 9/6256 |

OTHER PUBLICATIONS

Krishnaraj A. et al., "Simulating Dual-Energy X-Ray Absorptiometry in CT Using Deep-Learning Segmentation Cascade", Journal of the American College of Radiology, Elseveir, Amsterdam, NL, vol. 16, No. 10, Oct. 2019, pp. 1473-1479.

Chen L. et al., "Measuring Bone Density Connectivity Using Dual Energy X-Ray Absorptiometry Images", International Journal of Fuzzy Logic and Intelligent Systems, vol. 17, No. 4, Dec. 2017, pp. 235-244.

Deniz C. et al., "Segmentation of the Proximal Femur from MR Images using Deep Convolutional Neural Networks", Arxiv.org, Cornell University Library, 201 Olin Library Cornell University Ithaca, NY 14853, Apr. 20, 2017. pp. 1-13.

European Search Report (Application No. 20177226.6) dated Oct. 15, 2020.

Second Examination Report in Australian Application No. 2019204380, dated May 20, 2020.

Mehta et al., "Y-Net: Joint Segmentation and Classification for Diagnosis of Breast Biopsy Images", International Conference on Medical Image Computing and Computer-Assisted Intervention, 2018.

* cited by examiner

METHOD AND SYSTEM FOR MACHINE LEARNING CLASSIFICATION BASED ON STRUCTURE OR MATERIAL SEGMENTATION IN AN IMAGE

FIELD OF THE INVENTION

The present invention relates to a computer vision system and method, employing machine learning and in particular deep neural networks, for classifying (and monitoring changes in) an image (such as a medical image), based on structural or material segmentation. Possible medical imaging applications include Computed Tomography (CT), Magnetic Resonance (MR), Ultrasound, HRpQCT (High-Resolution peripheral Quantitative Computed Tomography), and Pathology Scanner imaging.

BACKGROUND

Computer vision and image processing techniques have been applied to medical image analysis. Some computer-aided systems achieve the analysis with two steps: segmentation and quantitative calculation. Segmentation is the process of segmenting (or differentiating) structures or objects in an image, such as a medical image, from one another by differentiating pixels (in 2D image) or voxels (in 3D image) in the image. Based on the segmentation, quantitative features such as volume, shape, and density are calculated. For example, lesion size and shape are calculated after the lesion has been segmented in a brain CT or MRI scan; the bone mineral density may be calculated after the femoral neck is segmented in a hip DXA (dual-energy x-ray absorptiometry) scan. A doctor may make a diagnosis or treatment decision after he or she has compared such calculated values with healthy reference data.

For example, a T-score is the standard score of a patient's bone mineral density compared to the young normal reference mean. The WHO (World Health Organization) defines osteoporosis as a T-score of −2.5 or lower, that is, a bone density that is two and a half standard deviations or more below the mean of a 30-year-old healthy man/woman.

The segmentation may be achieved manually, semi-manually, or automatically. In an example of manual segmentation, a user operates a computer to move a rectangular box over a hip DXA scan and thereby select the region of the femoral neck.

Semi-manual segmentation may be performed by an image processing program employing a user's initialisation or input. For example, a user may operate a computer to draw an approximate bone boundary on a wrist CT scan; the program then adjusts the approximate boundary into a contour that segments bone from the surrounding tissues.

Automatic segmentation may be performed by utilizing the features of the object of interest, such as intensity values, edges and shapes. In one existing example, a voxel-value based thresholding method is used to segment bone from the surrounding tissues in CT scans. Some other programs use machine learning algorithms to train a classifier to segment abnormal tissues in medical images. For example, a feature-based machine learning algorithm, such as a support vector machine and a decision tree, may be used as a classifier by using tumour images and normal images as training data. The trained classifier slides through the new image "window" by "window" to segment any image regions of tumour tissues.

Machine learning algorithms have shown promising accuracy and efficiency in this field. However, it is a significant challenge to both collect sufficient training data and to annotate the training data. The training images must be annotated by experts, which is a tedious and time-consuming process. Moreover, in some applications, it may be very difficult or nearly impossible to accurately annotate the training images, even for experts. For example, in bone quality assessment, a transitional zone exists at any sample composed of both cortical and trabecular bones. The transitional zone comprises the inner cortex adjacent to the medullary canal and trabeculae abutting against the cortex contiguous with the endocortical surface. The transitional zone is a site of vigorous bone remodelling. It is important to identify and segment this region in bone microstructure assessment but, owing to limitations in image resolution, it is essentially impossible for an expert to annotate this region both accurately and consistently. Without annotated images as training data, the segmentation model cannot be trained.

In the last few years, deep learning or deep neural networks have outperformed human in many visual recognition tasks such as natural image classification. In an exemplary CNN (Convolutional Neural Network) implementation, the network comprises input layer, hidden layers, and an output layer. An image is fed into the network through the input layer. The image is sampled and applied with convolutional operations to generate hidden layers. The output of each layer is used as input to the next layer in the network. The output layer is fully connected at the end that will output a classification result. Training data are images with classification labels. The training process obtains the parameters of the neural network. After the training is finished, a new image will be processed by the neural network with the obtained parameters to generate a classification result. For example, a deep neural network algorithm may be used to train a model to determine the condition (for example, no, mild, moderate, severe) of diabetic retinopathy from OCT (Optical Coherence Tomography) images.

However, this end-to-end solution brings two problems in clinical practices. First, the end-to-end solution is a black box: the input is the medical image, and the output the classification of diseases or conditions. It is difficult to interpret the process whereby the neural network makes its decision—so it is difficult for the user to assess the reliability of the classification results. Secondly, this solution requires a substantial amount of training data. As discussed above, in medical applications annotating or labelling the training data is a tedious and time-consuming process. Collecting enough training data for each category of each type of classification result thus poses a significant challenge.

SUMMARY

According to a first aspect of the invention, there is provided a system for classifying a structure or material in an image of a subject, comprising:
   a segmenter configured to form one or more segmentations of a structure or material in an image (comprising, for example, a medical image) and generate from the segmentations one or more segmentation maps of the image including categorizations of pixels or voxels of the segmentation maps assigned from one or more respective predefined sets of categories;
   a classifier that implements a classification machine learning model configured to generate, based on the segmentations maps, one or more classifications and to assign to the classifications respective scores indicative of a likelihood that the structure or material, or the subject, falls into the respective classifications; and an output for outputting a result indicative of the classifications and scores.

In an embodiment, the classifier generates the one or more classifications based on the segmentations maps and non-image data pertaining to the subject.

The system may be configured to train the classification machine learning model.

In an embodiment, the segmenter comprises:
i) a structure segmenter configured to generate structure segmentation maps including categorizations of the pixels or voxels assigned from a predefined set of structure categories,
ii) a material segmenter configured to generate material segmentation maps including categorizations of the pixels or voxels assigned from a predefined set of material categories, and/or
iii) an abnormality segmenter configured to generate abnormality segmentation maps including categorizations of the pixels or voxels assigned from a predefined set of abnormality or normality categories.

In an example, the structure segmenter is configured to employ a structure segmentation machine learning model to generate the structure segmentation maps, the material segmenter is configured to employ a material segmentation machine learning model to generate the material segmentation maps, and the abnormality segmenter is configured to employ an abnormality segmentation model to generate the abnormality segmentation maps. The structure segmenter may be configured to train the structure segmentation machine learning model, the material segmenter to train the material segmentation machine learning model, and/or the abnormality segmenter to train the abnormality segmentation model.

In an embodiment, the system further comprises a segmentation map processor configured to process the segmentation maps before the segmentation maps are input by the classifier. In an example, the segmentation map processor is configured to down-sample the segmentation maps.

In an embodiment, the classification machine learning model comprises a neural network, a support vector machine, a decision tree, or a combination thereof. For example, the classification machine learning model may comprise a neural network that includes convolutional neural network layers and fully-connected neural network layers.

In an embodiment, the image is a medical image, and the classifications correspond to probabilities that the structure or material, or the subject, will sustain a specified condition or symptom in respective timeframes. On an example, the timeframes include a shorter-term timeframe, a longer-term timeframe, and at least one intermediate-term timeframe intermediate the shorter-term timeframe and the longer-term timeframe. In another example, the condition or symptom is bone fracture.

In an embodiment, the image is a medical image, and the classifications correspond to probabilities that the structure or material, or the subject, will sustain respective conditions or symptoms. In an example, the conditions or symptoms are bone conditions.

In an embodiment, the image is a medical image, and the classifications correspond to probabilities of respective rates of disease or pathology progression. For example, the classifications may comprise classifications corresponding any one or more of: stable, modest deterioration, and accelerated deterioration.

In an embodiment, the image is a medical image, and the classifications correspond to probabilities of efficacy of respective treatment options. For example, the treatment options may include an antiresorptive treatment and/or an anabolic treatment.

In an embodiment, the image is a medical image, and the classifications correspond to respective medical conditions. For example, the medical conditions may include any one or more of: osteomalacia, tumour, osteonecrosis and infection.

In an embodiment, the classification machine learning model is a model trained with image data and non-image data relating to training subjects, and generates the respective scores based on image data (typically constituting one or more images) and non-image data relating to the subject.

According to a second aspect of the invention, there is provided a computer-implemented method for classifying a structure or material in an image of a subject, comprising:
forming one or more segmentations of a structure or material in an image;
generating from the segmentations one or more segmentation maps of the image including categorizations of pixels or voxels of the segmentation maps assigned from respective predefined sets of categories of the structure or material;
using a classification machine learning model to generate, based on the segmentations maps, one or more classifications and to assign to the classifications respective scores indicative of a likelihood that the structure or material, or the subject, falls into the respective classifications; and
outputting a result indicative of the classifications and scores.

In an embodiment, the classification machine learning model is used to generate the one or more classifications based on the segmentations maps and non-image data pertaining to the subject.

The method may include training the classification machine learning model.

In an embodiment, forming the one or more segmentations comprises:
i) generating structure segmentation maps including categorizations of the pixels or voxels assigned from a predefined set of structure categories,
ii) generating material segmentation maps including categorizations of the pixels or voxels assigned from a predefined set of material categories, and/or
iii) generating abnormality segmentation maps including categorizations of the pixels or voxels assigned from a predefined set of abnormality or normality categories.

For example, the method may include employing a structure segmentation machine learning model to generate the structure segmentation maps, a material segmentation machine learning model to generate the material segmentation maps, and an abnormality segmentation model to generate the abnormality segmentation maps. In particular, the method may include training the structure segmentation machine learning model, the material segmentation machine learning model, and/or the abnormality segmentation model.

According to a third aspect of the invention, there is provided a computer-implemented diagnostic method, comprising the method of the second aspect.

According to a fourth aspect of the invention, there is provided a computer-implemented method for training a classification machine learning model for classifying a structure or material in an image of a subject, the method comprising:

dividing annotated segmentation maps and annotated non-image data into a training set and a testing set (such that, as a result, the training set and the testing each include some annotated segmentation maps and some annotated non-image data), the annotated segmentation maps obtained by segmenting one or more images;

implementing a classification machine learning model, including initializing parameters of the classification machine learning model;

updating the parameters of the classification machine learning model by running a learning algorithm on the training data;

testing the classification machine learning model on the testing data;

evaluating whether the classification machine learning model has satisfactory performance; and when the performance is found to be satisfactory, outputting the classification machine learning model for deployment or flagging the classification machine learning model as fit for deployment.

This aspect may be used in conjunction or in combination with (or as a part of) the second aspect, such as to train the classification machine learning model of the second aspect.

The method may include segmenting the one or more images (such as in the course of generating the annotated segmentation maps).

In an embodiment, the method includes, when the performance is found to be unsatisfactory, collecting more image and non-image data for training the classification machine learning model.

The classification model can be trained by various machine learning algorithms, so may comprise—for example—a neural network, a support vector machine, a decision tree, or a combination thereof.

Thus, in one embodiment, the classification machine learning model comprises a neural network having a plurality of layers comprising artificial neurons, wherein the parameters comprise layer numbers, neuron numbers, neuron weights, and neuron function parameters; and testing the classification machine learning model includes testing the classification machine learning model on the testing data.

In an embodiment, updating the parameters includes determining a gradient of a loss function.

In an embodiment, the images are medical images and the non-image data comprise clinical records.

In an embodiment, the method includes dividing the annotated segmentation maps and the annotated non-image data into the training set, a development set and the testing set, and using the development data to investigate the learning procedure and to tune the parameters (and, when the classification machine learning model comprises a neural network, tune the layers).

According to a fifth aspect of the invention, there is provided a computer program comprising program code configured, when executed by one of more computing devices, to implemented the method of any one or more of the second to fourth aspects. According to this aspect, there is also provided a computer-readable medium, comprising such a computer program.

It should be noted that any of the various individual features of each of the above aspects of the invention, and any of the various individual features of the embodiments described herein including in the claims, can be combined as suitable and desired.

BRIEF DESCRIPTION OF THE DRAWINGS

In order that the invention may be more clearly ascertained, embodiments will now be described by way of example with reference to the following drawing, in which.

DETAILED DESCRIPTION

Figure 1:
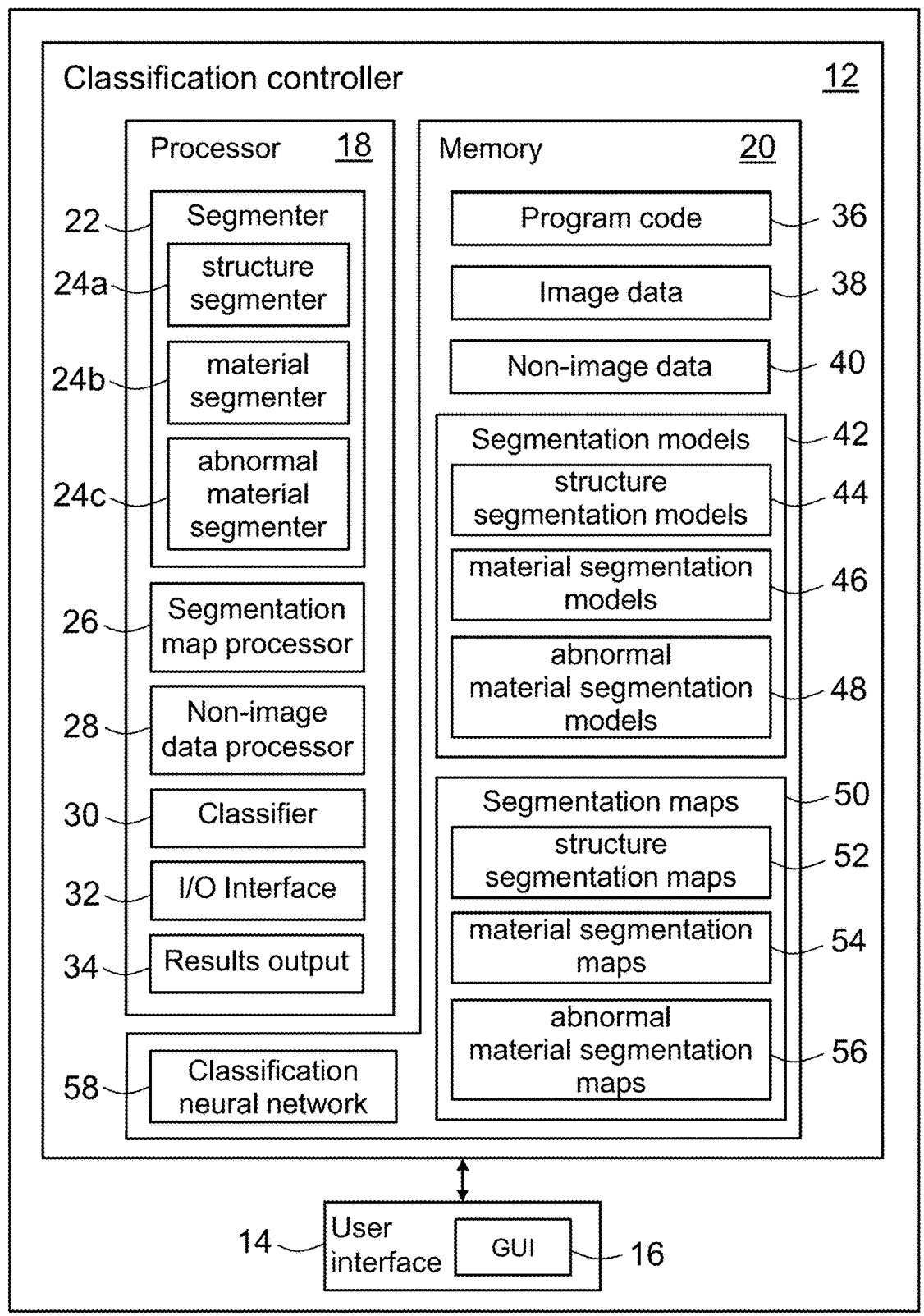
FIG. 1 is a schematic view of a classification system according to an embodiment of the present invention.

FIG. 1 is a schematic view of a classification system 10 for classifying a structure or material in a medical image (based on structural and material segmentation), according to an embodiment of the present invention.

Referring to FIG. 1, system 10 comprises a classification controller 12 and a user interface 14 (including a GUI 16). User interface 14 is provided for representing information to a user and for receiving input (including feedback) from a user; it typically comprises one or more displays (on one or more of which may be displayed the GUI 16), a web browser, a keyboard and a mouse, and optionally a printer. Classification controller 12 includes at least one processor 18 and a memory 20. System 10 may be implemented, for example, as a combination of software and hardware on a computer (such as a personal computer or mobile computing device), or as a dedicated image segmentation system. System 10 may optionally be distributed; for example, some or all of the components of memory 20 may be located remotely from processor 18; user interface 14 may be located remotely from memory 20 and/or from processor 18. For example, system 10 may be implemented in a service-oriented architecture, with its components communicating with each other over a communication network such as a LAN (local area network), WAN (wide area network) or the internet System 10 may be deployed in the cloud, and its use shared by users at different locations.

In certain other embodiments, system 10 is implemented as a standalone system (of software and hardware) or as standalone software executable by a computer, and deployed in one location; for example, system 10 may be deployed in a hospital, medical clinic or other clinical setting.

Memory 20 is in data communication with processor 18, and typically comprises both volatile and non-volatile memory (and may include more than one of each type of memory), including RAM (Random Access Memory), ROM and one or more mass storage devices.

As is discussed in greater detail below, processor 18 includes a segmenter 22 (which includes a structure segmenter 24a, a material segmenter 24b, and an abnormal segmenter in the form of an abnormal material segmenter 24c), an segmentation map processor 26, and a non-image data processor 28. Processor 18 also includes a classifier 30, an I/O interface 32 and a results output 34.

Memory 20 includes program code 36, image data 38, non-image data 40, segmentation models 42 (including, in this example, structure segmentation models 44, material segmentation models 46, and abnormality segmentation models in the form of abnormal material segmentation models 48), segmentation maps 50 (including, in this example, structure segmentation maps 52, material segmentation maps 54, and abnormality segmentation maps in the form of abnormal material segmentation maps 56). Structure segmenter 24a, material segmenter 24b and abnormal material segmenter 24c train the respective segmentation models 44, 46, 48, and use segmentation models 44, 46, 48 to perform segmentation on incoming images and generate structure segmentation maps 52, material segmentation maps 54, and abnormal material segmentation maps 56, respectively.

Memory 20 also includes a classification machine learning model in the form of a classification neural network 58, which is trained and used by classifier 30 to perform classification by using segmentation maps 50 and non-image data 40. Classification controller 12 is implemented, at least in part (and in some embodiments entirely), by processor 18 executing program code 36 from memory 20.

It should be noted that, as the present embodiment relates to the classifying of structures and/or materials in a medical image, abnormal material segmenter 24c may also be referred to as an abnormal tissue segmenter, and abnormal material segmentation maps 56 may also be referred to as abnormal tissue segmentation maps.

In broad terms, I/O interface 32 is configured to read or receive medical image data and non-image data pertaining to a subject, and to store these data as image data 38 and non-image data 40 of memory 20 for processing. Image data 38 is typically in the form, in this embodiment, of a medical image of—for example—a region of the body of a subject Non-image data 40 typically includes subject or patient information from various structured and non-structured data sources, collected throughout a subject's medical consultations, treatment and follow-up consultations. Subject structured data may include basic subject information such as sex, age, weight, height; laboratory test results such as blood test results and DNA test results; treatment data such as the types of medication and dosage; and questionnaire data such as smoking and drinking habits and fracture history. Subject unstructured data may include text documents of laboratory results, doctors' notes, and radiological reports. Non-image data 40 may in a variety of formats, such as numerical data, text, voice, and video.

Segmenter 22 processes image data 38 (constituting one or more medical images) and uses structure segmentation models 44, material segmentation models 46 and abnormal material segmentation models 48 to generate—from image data 38—structure segmentation maps 52, material segmentation maps 54 and abnormal material segmentation maps 56, respectively, which characterize image data 38 in different ways. Classifier 30 then inputs the resulting segmentation maps 50 and non-image data 40, and generates therefrom results in the form of a classification output. The classification output is, in this embodiment, presented to users or used for further analysis via I/O interface 32 and at either results output 34 and/or user interface 14.

The classification output of classifier 30 (in this embodiment, generated using classification neural network 58) comprises a respective condition score for each of one or more classifications (and preferably for each of a plurality of possible classifications). Each score represents a predicted likelihood that the subject falls into the corresponding classification. In the present example of bone fragility assessment, the classifications are "negligible fracture risk", "imminent fracture risk", "intermediate-term fracture risk", and "long-term fracture risk". The classification output is described in more detail below.

In an alternative embodiment, the classifier outputs a respective disease progression score for each of one or more condition progression states. Each score represents a predicted likelihood that a current condition will progress to another condition. For example, in bone fragility assessment, the disease progressions may include "stable", "modest deterioration", and "accelerated deterioration".

In still another embodiment, the classifier outputs a respective treatment score for each of multiple treatment options. Each score represents a predicted likelihood that the treatment is the most efficient for the patient. For example, in a bone fragility assessment, the treatment options may include "antiresorptive", "anabolic", and "antiresorptive+anabolic".

In a further embodiment, the classification output comprises a score for each of one or more possible classifications corresponding to known medical conditions or pathologies. For example, in a bone fragility assessment, these classifications could be "osteomalacia", "tumour", "osteonecrosis" and "infection". In such an embodiment, the resulting scores represent the degree to which the (e.g. bone) sample of the subject conforms to that classification/condition. If only one classification has a significant score, or one classification has a score that is significantly greater than all other scores, that classification may be regarded as a diagnosis, or suggested diagnosis, of the corresponding condition or pathology.

In certain embodiments, the classification output comprises two or more sets of such scores (selected from the aforementioned examples or otherwise).

Returning to FIG. 1, as will be appreciated by the skilled person in this art, image data 38—constituting one or more medial images—comprises data generated by one or more of a variety of medical image modalities (such as HRpQCT, or High-Resolution peripheral Quantitative Computed Tomography) implemented by one or more medical imaging devices (such as a HRpQCT scanner). Each of these devices scans a sample (whether in vivo or in vitro) and creates a visual representation, generally of a portion of the interior of a subject's body. The medical images may depict, for example, a part of a body or a whole body of a subject (e.g. the brain, the hip or the wrist). The medical images might be acquired by scanning the same sample or body part using different imaging modalities, as different imaging modalities may reveal different characteristics of the same sample or body part. The medical images might be acquired by scanning different body parts using the same image modalities, as different body parts of the same patients might provide different insights towards a better diagnosis of diseases or conditions. For example, in bone fragility assessment, both the wrist and the leg of a patient may be scanned by an HRpQCT scanner (or indeed acquired by scanning the different samples or body parts using different imaging modalities) to provide information for use in assessing a subject's bone quality.

The image data 38 may constitute a 2D (two-dimensional) image that may be represented as a 2D array of pixels, or a 3D (three-dimensional) image that may be represented as a 3D array of voxels. For convenience, the medical images described below are 3D images that may be represented as a 3D array of voxels.

As mentioned above, the one or more received medical images, stored in image data 38, are segmented by segmenter 22, using trained segmentation models 42, into respective segmentation maps 50. Each segmentation map 52, 54, 56 characterizes the respective medical image differently. A structure segmentation map 52 represents the medical image as one or more different anatomical structures from a predefined set of structures. For example, a wrist CT scan may be segmented into compact cortex, transitional zone, and trabecular region. Material segmentation map 54 represents the medical image into multiple different materials from a predefined set of materials. For example, a wrist CT scan might be segmented into mineralized material, fully mineralized material, red marrow in the trabecular region, and yellow marrow in the trabecular region. An abnormal material segmentation map 56 represents the medical image as normal material and abnormal material (or, in this example, normal tissue and abnormal tissue). For example, a tumour or fracture might be segmented from a wrist CT scan and represented in an abnormal material segmentation map 56 as 'abnormal'.

Segmentation maps 50 are inputted into classifier 30, in combination with non-image data 40. Classifier 30 generates one or more classification outputs based on segmentation maps 50 and the non-image data 40. Input data of classifier 30 is generally multi-dimensional, so classifier 30 is implemented with machine learning algorithms, such as a neural network, support vector machine, decision tree, or a combination thereof.

In this embodiment, classifier 30 employs or is implemented as classification neural network 58 (though in other embodiments, other machine learning algorithms may be acceptable), including—in this example—convolutional neural network layers and fully-connected neural network layers. Classification neural network 58 is trained with training data, as is described below.

As mentioned above, the ultimate classification output is outputted by system 10 to a user via results output 34 or user interface 14. The classification output may optionally include a visual presentation of one or more of the corresponding segmentation maps 50. Segmentation maps 50 may be presented in case they can assist a user in interpreting the classification output, such as in assessing the reliability of the results.

Figure 2:
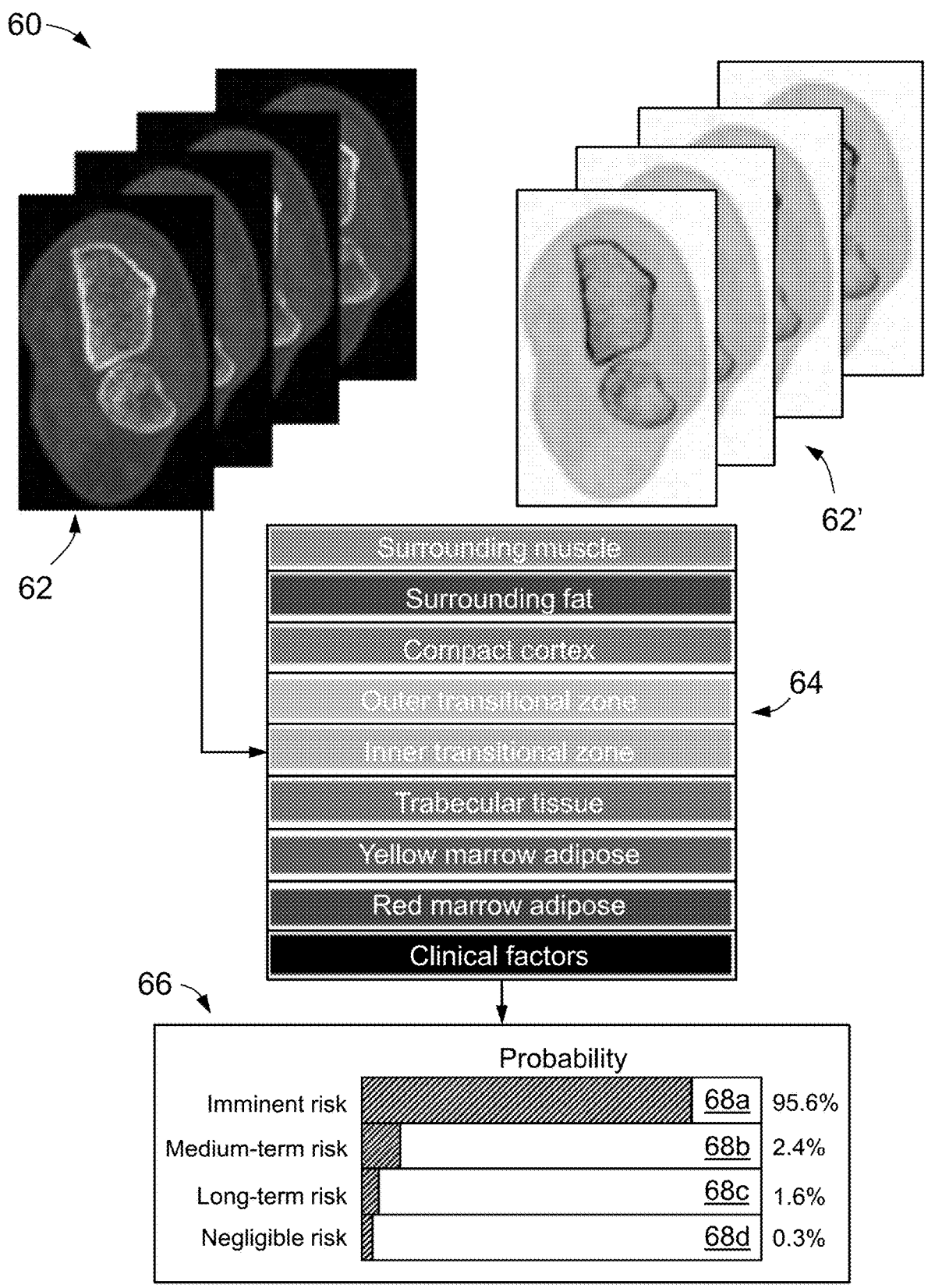
FIG. 2 is a high-level schematic diagram illustrating the operation of the classification system of FIG. 1, in calculating bone fracture risk of a subject from a medical imaging scan.

FIG. 2 is a high-level schematic diagram 60 illustrating the operation of system 10 in calculating bone fracture risk of a subject from a medical imaging scan, in this example a wrist HRpQCT scan 62 (also shown in negative at 62'). As shown in FIG. 2, system 10 receives the wrist HRpQCT scan 62 comprising a plurality of slices. (As will be appreciated by the skilled person, an HRpQCT scan can comprise 100 or more slices, but four slices are depicted in the figure for simplicity.)

Segmenter 22 segments scan 62 into a structure segmentation map 52 in which the scan is segmented into compact cortex, outer transitional zone, inner transitional zone, and trabecular region. Segmenter 22 segments scan 62 into material segmentation map 54, in which scan 62 is segmented into surrounding muscle, surrounding fat, yellow marrow adipose, and red marrow adipose. Data 64 comprising segmentation maps 52, 54, abnormal material segmentation maps 56 and non-image data 40 (e.g. clinical factors including sex and age) are processed by trained classifier 30 to generate classification outputs. The classification outputs include segmentation maps 52, 54 and a table or report 66. Table or report 66 includes, in numerical and/or graphical form, fracture probabilities in each category of fracture risk: imminent fracture risk 68a (fracture within two years: t<2 y), intermediate-term fracture risk 68b (fracture within two to five years: 2≤t<5 y), long-term fracture risk 68c (fracture in five to ten years, 5≤t≤10 y), and negligible fracture risk 68d. In the illustrated example, the probability that the wrist is at risk of fracture within two years is 95.6%, that the wrist is at a risk of fracture in two to five years 2.4%, that the wrist is at a risk of fracture in five to 10 years 1.6%, and that the wrist is at negligible risk of fracture is 0.3%. In other words, the probability that the subject will not have a wrist fracture in the next five years (either because the wrist has negligible risk of fracture or because there is only a long-term fracture risk) is only 4.4%. Table or report 66 does not include a diagnosis (e.g. that the subject has osteoporosis), but it will be appreciated that these probabilities may be of great value, including—for example—to prompt the subject to pursue a diagnosis, such as by undergoing medical examination or consultation.

Figure 3:
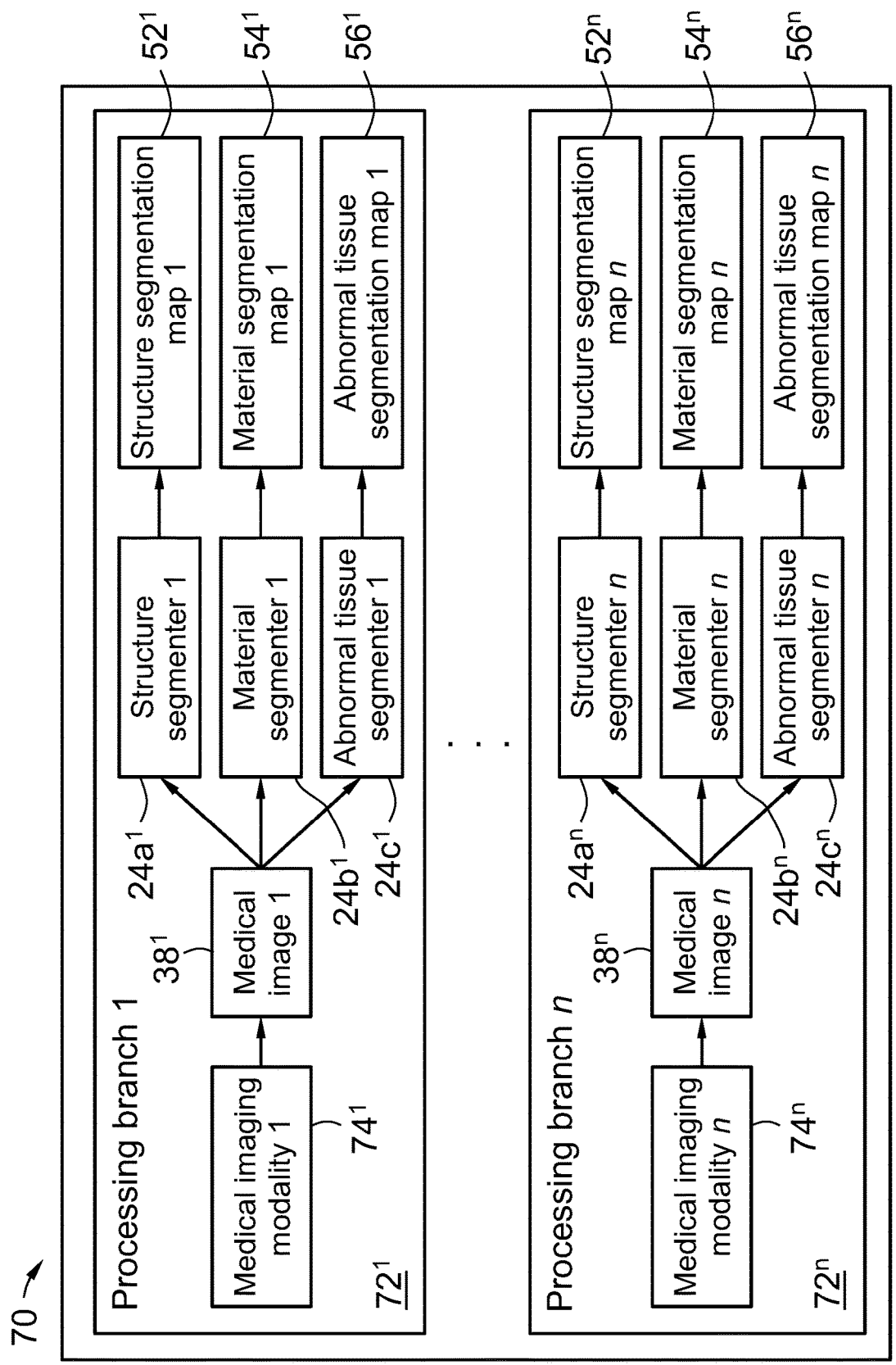
FIG. 3 is a schematic view of the operation of the segmenter of the classification system of FIG. 1.

FIG. 3 is a schematic view at 70 of the operation of segmenter 22. Segmenter 22 is configured to receive input includes one or more medical images (from image data 38) and to process the images so as to generate segmentation maps 50. The medical images might be acquired using the same imaging modality by scanning different body parts of a patient. For example, in some applications of assessing bone quality, both wrist and leg of a patient might be scanned by an HRpQCT scanner for the assessment. The medical images might be acquired using different imaging modalities by scanning the same or different body parts of a patient. For example, in some other applications of assessing bone quality, both the wrist HRpQCT scan and the hip DXA scan of a patient are acquired for the assessment (though again bearing in mind that the medical images may be acquired by scanning the different samples or body parts using other imaging modalities).

Referring to FIG. 3, segmenter 22 implements one or more processing branches 1 to n, (labelled $72^1, \ldots, 72^n$ in the figure) corresponding to medical images 1 to n of the subject (labelled $38^1, \ldots, 38^n$). In the case of plural processing branches, medical images $38^1, \ldots, 38^n$ may be due to—for example—different imaging modalities (labelled $74^1, \ldots, 74^n$), as is the case in the illustrated example, different body parts, different scans of a single body part, or a combination two or more of these. Respective segmentation branches $72^1, \ldots, 72^n$ are configured to receive an image, to segment the image according to image type (such as with different program code 36), and to generate the branch output (comprising the segmentation maps 50 of the input image).

To process a respective input medical image, segmenter 22 is configured first to select a processing branch of processing branches 1 to n according to the type of the input image. Segmenter 22 ascertains the type of image according to the sample (e.g. scanned body part) and imaging modality, information that can be determined from the respective image, including from metadata stored in a header file of the medical image and/or from the file type. For example, the information of scanned body part and imaging modality may be accessed from the metadata.

Each input medical image 1 to n is processed by one or more of three segmentation programs (viz. structure segmenter 24a, material segmenter 24b, and abnormal material segmenter 24c) into the corresponding segmentation maps 52, 54, 56. Segmenter 22 thus employs up to n instances each of segmenters 24a, 24b, 24c (labelled $24a^1, \ldots, 24a^n$, $24b^1, \ldots, 24b^n$, and $24c^1, \ldots, 24c^n$, respectively), either in parallel or sequentially, though the number of such instances of each segmenter 24a, 24b, 24c (being from 0 to n in each case) may differ.

Structure segmenter 24a, material segmenter 24b, and abnormal material segmenter 24c may generate respective segmentation maps in each processing branch $72^1, \ldots, 72^n$. In FIG. 3, for example, structure segmenter 24a, material segmenter 24b, and abnormal material segmenter 24c generate respective segmentation maps corresponding to medical imaging modalities 1 to n; the resulting structure segmentation maps, material segmentation maps and abnormal tissue segmentation maps are correspondingly labelled structure segmentation maps $52^1$, ..., $52^n$, the material segmentation maps $54^1$, ..., $54^n$ and the abnormal tissue segmentation maps $56^1$, ..., $56^n$. It should be noted, however, that in some applications it may not be possible or desirable to generate all three types of segmentation map. This may be due, for example, to the limitations of the images, of the imaging modalities, or of segmenters 24a, 24b, 24c (arising, for example, from limitations in segmenter training data).

Structure segmenter 24a, material segmenter 24b, and abnormal material segmenter 24c assign to each voxel of these segmentation maps 50 one or more 'types' (or 'categories') from respective predetermined sets of types (or categories). Thus, in this embodiment structure segmenter 24a assigns a respective structure type (from a predefined set of structure types) to each voxel in the scan. For example, a wrist HRpQCT scan is segmented into a structure segmentation map 52 in which each voxel in the scan is assigned a structure type (or category) from the set of "surrounding tissues", "compact cortex", "transitional zone", and "trabecular region".

Material segmenter 24b assigns a respective material type (from a predefined set of material types) to each voxel. For example, in this embodiment, material segmenter 24b segments a wrist HRpQCT scan into a material segmentation map 54 in which each voxel in the scan is assigned a material type from the set of "mineralised material", "fully mineralised material", "red marrow adipose", and "yellow marrow adipose".

Abnormal material segmenter 24c assigns a respective abnormality or normality type (from a predefined set of abnormalities or normality types, such as a set comprising "normal" and "abnormal") to each voxel. For example, in this embodiment, abnormal material segmenter 24c segments a wrist HRpQCT scan into an abnormal tissue segmentation map 56 in which each voxel in the scan is assigned either "normal" or "abnormal". Optionally, in certain other embodiments, abnormal material segmenter 24c can distinguish different types of abnormality, and the predefined set of abnormality or normality types may include—in addition to "normal"—and one or more specific abnormalities particular to the sample type under examination; if the sample is bone, these may include, for example, "fracture crack" or "bone tumour". In such an embodiment, the set may optionally include "abnormal" for cases in which abnormal material segmenter 24c cannot determine a specific type of abnormality.

In some implementations, structure segmenter 24a, material segmenter 24b, and abnormal material segmenter 24c assign respective types with confidence limits or probabilities to each voxel in the medical image. In some other implementations, structure segmenter 24a, material segmenter 24b, and abnormal material segmenter 24c may assign a plurality of types (each optionally with a confidence limit or probability) to each voxel in the medical image. For example, structure segmenter 24a—when segmenting a wrist HRpQCT scan—may assign both "transitional zone" and "trabecular region" to ambiguous voxels, but with respective (and typically different) confidence limits or probabilities.

Segmenter 22 generates segmentation maps 50 by using the trained segmentation models 42 (including structure segmentation models, material segmentation models and abnormal material segmentation models). The segmentation models are trained using machine learning algorithms (such as a neural network, a support vector machine, a decision tree, or a combination thereof). In this embodiments, the segmentation models are trained using deep neural networks that comprises multiple layers include convolutional neural network layers, fully connected neural network layers, normalisation layers, and multiplicative layers.

Segmenter 22 may also (or alternatively) perform segmentation using non-machine learning based methods, such as a method based on the location of edges, corners, and transitional slopes, or on global features such as histogram and intensity values of the image. For example, U.S. Patent Application Publication No. 2012/0232375 A1 ("Method and System for Image Analysis of Selected Tissue Structures") discloses a method for segmenting the transitional zone between the compact cortical and trabecular region from a wrist CT scan, based on local and global features of a bone: in many applications, it would be suitable to implement this method in segmenter 22.

Figure 4:
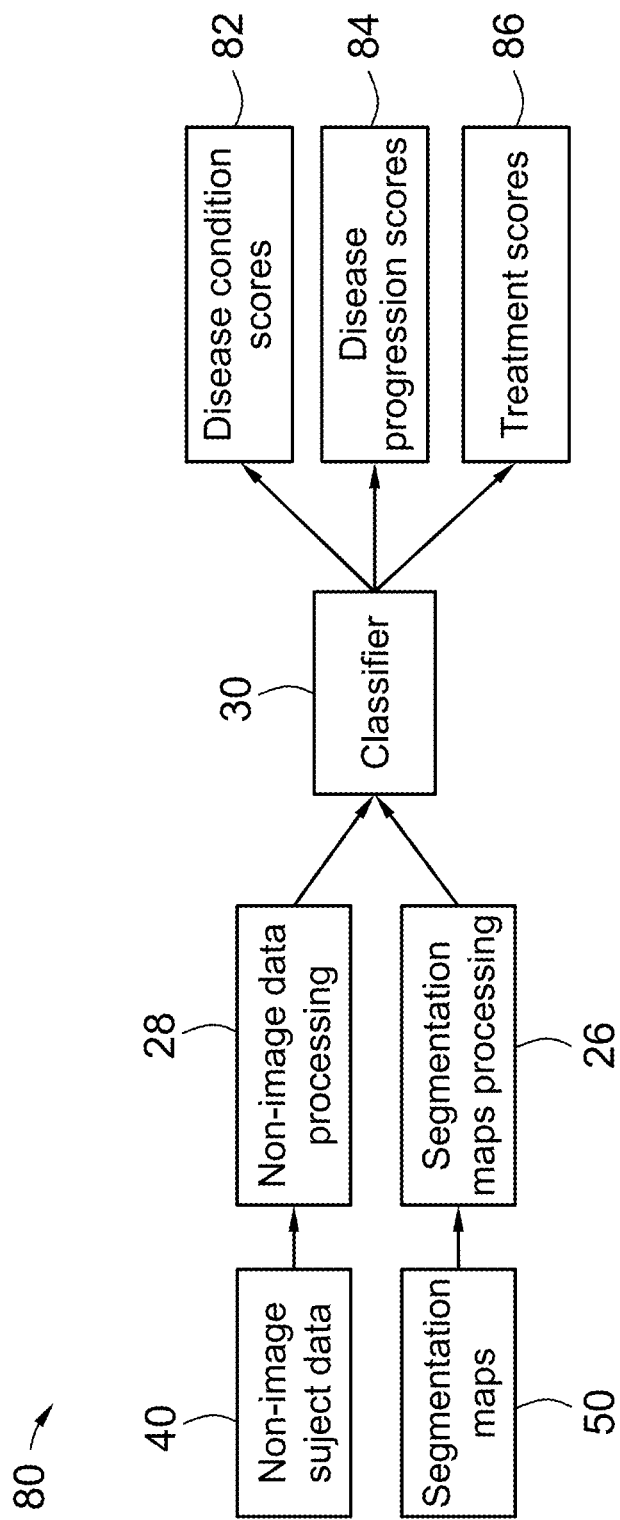
FIG. 4 is a schematic illustration of the operation of classifier of the classification system of FIG. 1.

FIG. 4 is a schematic illustration of the operation 80 of classifier 30. Classifier 30 is configured to receive input that includes segmentation maps 50 (generated by segmenter 22) and non-image subject data 40, and to process that input so as to generate one or more classification results.

However, both the segmentation maps 50 and non-image subject data 40 are processed before being passed to classifier 30 by segmentation map processor 26 and non-image data processor 28, respectively. For example, in some implementations, it may be expedient to down-sample segmentation maps 50 into lower resolution maps, such as to allow faster image processing by classifier 30; such processing, if desired or required, is performed by segmentation map processor 26. In some implementations, segmentation map processor 26 sets the type of any voxels (in a particular segmentation map) that have been assigned more than one type (though typically with different confidence limits or probabilities), such as by assigning to the voxel the type that has the higher or highest probability.

Non-image data may include structured and unstructured data. Non-image data processor 28 is configured to employ a variety of techniques to process any structured data by extracting features from it, in each case according to the structure and form of the data. For example, structured data are typically stored and maintained in structured data storage such as database tables, .json files, .xml files and .csv files. Non-image data processor 28 extracts features from structured data by querying the required parameters and attributes from the data's respective sources.

Non-image data processor 28 processes unstructured data in two steps: firstly by converting it into structured data, then by extracting features from the converted data. The conversion method employed by non-image data processor 28 is specific to each source. For example, to convert a doctor's notes into structured data, non-image data processor 28 employs a trained model of optical character recognition (OCR) to convert the notes into text recognisable by a computer. Non-image data processor 28 then parses the converted text using keywords such as, in this example, "fractures", "pain", "fall", etc. Once the unstructured data has been converted into structured data, non-image data processor 28 then extracts features from the now structured data.

The processed non-image data 40 and segmentation maps 22 are passed to classifier 30, which uses these inputs to generate a classification outputs comprising classification score (such as disease condition scores 82, disease progression scores 84, and/or treatment scores 86).

Figure 5:
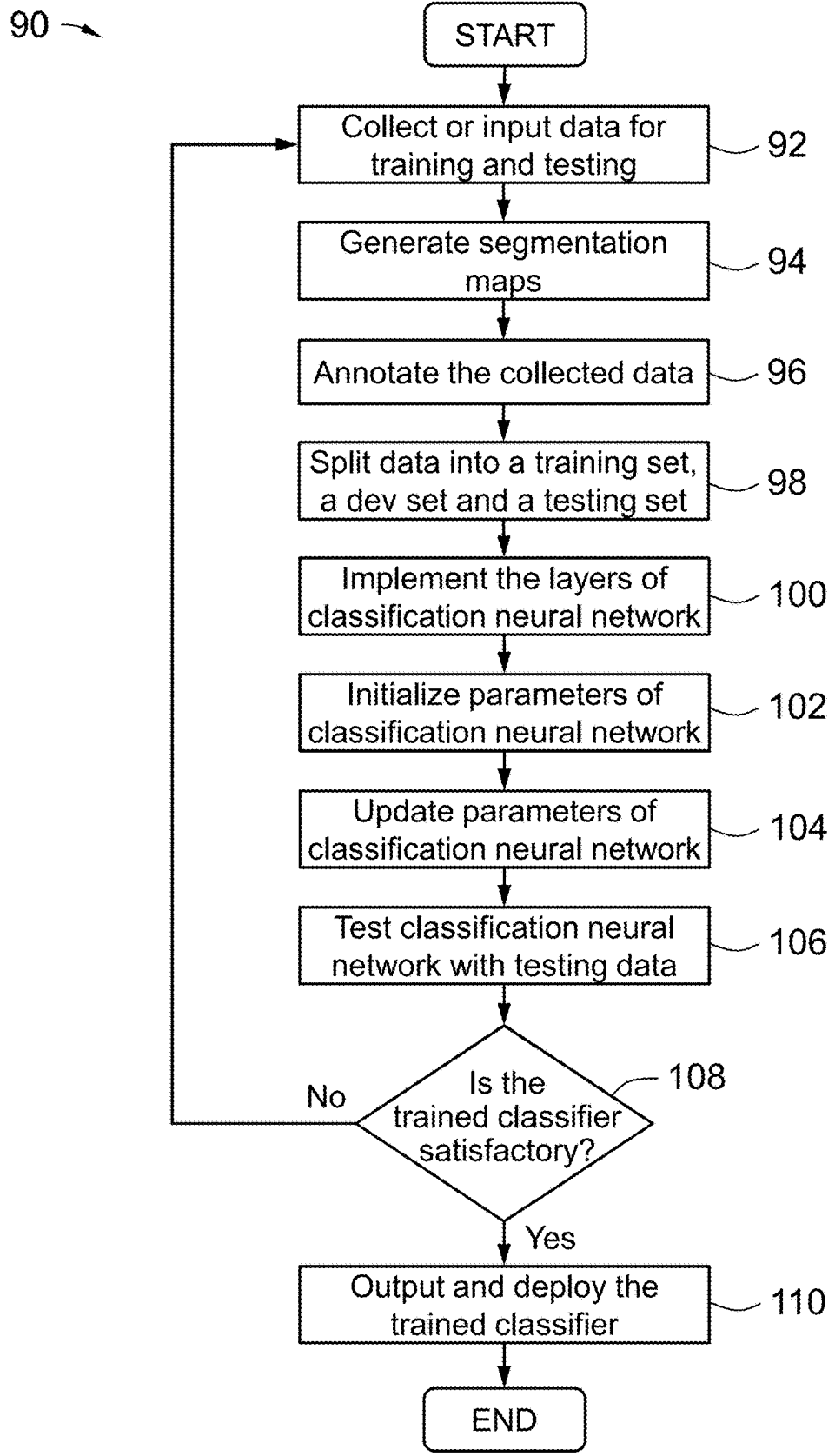
FIG. 5 is a flow diagram of the training of the classification neural network of the classification system of FIG. 1.

FIG. 5 is a flow diagram 90 of the training of classification neural network 58 of classifier 30 with a deep neural network, according to an embodiment of the present invention. As shown in the figure, at step 92, data—including medical image data and non-image data—are collected or input for training and testing. At step 94, the collected images are segmented by segmenter 22 so as to generate segmentation maps (as described above).

At step 96, the image data 38 and non-image data 40 are annotated with labels provided by qualified experts with domain knowledge. In a medical application, the training classification outputs may be determined based on subject clinical records. For example, if the classification output is to include a fracture probability score, then the training output is the timing (post-scan) of a fracture, ascertained from the subject's medical history—and, where no fracture is apparent, recorded as "negligible risk" (or some equivalent designation). If the classification output is to include a score for categories that correspond to known medical conditions, then the training output is the actual medical condition of the subject, also ascertained from the subject's clinical records.

At step 98, the data (comprising segmentation maps 50 and non-image data 40) is split into a training set, a development or 'dev' set (which may be omitted in some implementations), and a testing set, each for a different use. The training set is the data on which the learning algorithm is to be run; the dev set is the data used to tune the parameters; the testing set is the data to be used to evaluate the performance of the trained model.

At step 100, the layers of the deep neural network are implemented. Each layer consists of artificial neurons. An artificial neuron is a mathematical function that receives one or more inputs and sums them to produce an output. Usually, each input is separately weighted, and the sum is passed through a non-linear function. As the neural network learns, the weights of the model are adjusted in response to the error (the difference between the network output and the annotations) it produces until the error cannot be reduced further.

At step 102, the parameters of classification neural network 58—including layer numbers, neuron numbers, neuron weights, and neuron function parameters, etc.—are initialized. At step 104, the learning algorithm runs on the training data set to update the parameters of classification neural network 58. For example, the parameters might be updated by determining a gradient of a loss function. The loss function is calculated by the labelled classification output and output generated by classification neural network 58. The dev data may be used to investigate the learning procedure and tune the layers and parameters.

At step 106, classifier 30—provided with classification neural network 58—is tested on the testing data. At step 108, an evaluation is made as to whether the performance of classifier 30 is satisfactory. If the performance is unsatisfactory, processing returns to step 92 where more training data is collected.

If, at step 108, the performance is found to be satisfactory, processing continues at step 110, where the trained classifier 30 is outputted or flagged for deployment, or released for use. Processing then ends.

It will be understood to persons skilled in the art of the invention that many modifications may be made without departing from the scope of the invention, in particular it will be apparent that certain features of embodiments of the invention can be employed to form further embodiments.

It is to be understood that, if any prior art is referred to herein, such reference does not constitute an admission that the prior art forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A computer-implemented method for training a classification machine learning model for classifying a structure or material in an image of a subject, the method comprising:
dividing annotated segmentation maps of one or more images and annotated non-image data pertaining to the subject into a training set and a testing set, the annotated segmentation maps generated from one or more segmentations formed by segmenting each of the one or more images into one or more segmentations that correspond to respective structures or materials in the respective image;
(a) implementing a classification machine learning model for classifying a structure or material in an image of a subject, including initializing parameters of the classification machine learning model;
(b) updating the parameters of the classification machine learning model by running a learning algorithm on the training data;
(c) testing the classification machine learning model on the testing set;
(d) evaluating whether the classification machine learning model has satisfactory performance;
repeating steps (a) to (d) when the performance is found in step (d) not to be satisfactory; and
outputting the classification machine learning model for deployment as a trained classification machine learning model, or flagging the classification machine learning model as a trained classification machine learning model;
wherein each of the training and testing sets includes at least one of the annotated segmentation maps of the image and at least some annotated non-image data; and
each of the annotated segmentation maps corresponding to a respective image represents the image.

2. A method as claimed in claim 1, including, when the performance is found in step (d) not to be satisfactory, receiving and using more image and non-image data for training the classification machine learning model.

3. A method as claimed in claim 1, wherein the classification machine learning model comprises a neural network having a plurality of layers comprising artificial neurons, wherein the parameters comprise layer numbers, neuron numbers, neuron weights, and neuron function parameters.

4. A method as claimed in claim 1, including dividing the annotated segmentation maps and the annotated non-image data into the training set, a development set and the testing set, and using the development set to investigate the learning procedure and to tune the parameters.

5. A method as claimed in claim 1, including segmenting each of the one or more images into the one or more segmentations, wherein generating the annotated segmentation maps comprises:
i) generating structure segmentation maps of the respective image including categorizations of the pixels or voxels assigned from a predefined set of structure categories, ii) generating material segmentation maps of the respective image including categorizations of the pixels or voxels assigned from a predefined set of material categories, iii) generating structure segmentation maps of the respective image including categorizations of the pixels or voxels assigned from a predefined set of structure categories with a structure segmentation machine learning model, and/or iv) generating material segmentation maps of the respective image including categorizations of the pixels or voxels assigned from a predefined set of material categories with a material segmentation machine learning model.

6. A method as claimed in claim 1, further comprising down-sampling or otherwise processing the segmentation maps.

7. A method as claimed in claim 1, including segmenting each of the one or more images into the one or more segmentations, wherein generating the annotated segmentation maps comprises:
generating abnormality segmentation maps of the respective image including categorizations of the pixels or voxels assigned from a predefined set of abnormality or normality categories, or
generating abnormality segmentation maps of the respective image including categorizations of the pixels or voxels assigned from a predefined set of abnormality or normality categories with an abnormality segmentation model.

8. A method as claimed in claim 1, including segmenting each of the one or more images into the one or more segmentations, wherein generating the annotated segmentation maps comprises:
i) generating structure segmentation maps of the respective image including categorizations of the pixels or voxels assigned from a predefined set of structure categories, and generating material segmentation maps of the respective image including categorizations of the pixels or voxels assigned from a predefined set of material categories, or
ii) generating structure segmentation maps of the respective image including categorizations of the pixels or voxels assigned from a predefined set of structure categories with a structure segmentation machine learning model, and generating material segmentation maps of the respective image including categorizations of the pixels or voxels assigned from a predefined set of material categories with a material segmentation machine learning model.

9. A system for classifying a structure or material in an image of a subject, comprising:
a segmenter configured to segment an image into one or more segmentations that correspond to respective structures or materials in the image, and to generate from the segmentations one or more segmentation maps of the image including categorizations of pixels or voxels of the segmentation maps assigned from one or more respective predefined sets of categories;
a classifier that implements a trained classification machine learning model configured to generate, based on the segmentations maps, one or more classifications and to assign to the classifications respective scores indicative of a likelihood that the structure or material, or the subject, falls into the respective classifications; and
an output for outputting a result indicative of the classifications and scores;
wherein the trained classification machine learning model is a model trained according to the method of claim 1.

10. A classification machine learning model trained according to the method of claim 1.

11. A computer-implemented method for classifying a structure or material in an image of a subject, comprising:
segmenting an image into one or more segmentations that correspond to respective structures or materials in the image;
generating from the segmentations one or more segmentation maps of the image including categorizations of pixels or voxels of the segmentation maps assigned from respective predefined sets of categories of the structure or material;
using a trained classification machine learning model to generate, based on the segmentations maps, one or more classifications and to assign to the classifications respective scores indicative of a likelihood that the structure or material, or the subject, falls into the respective classifications; and
outputting a result indicative of the classifications and scores;
wherein the trained classification machine learning model is a model trained according to the method of claim 1.

12. A system for training a classification machine learning model for classifying a structure or material in an image of a subject, the system comprising a processor configured to:
divide annotated segmentation maps of one or more images and annotated non-image data pertaining to the subject into a training set and a testing set, the annotated segmentation maps obtained by segmenting each of the one or more images into one or more segmentations that correspond to respective structures or materials in the respective image;
(a) implement a classification machine learning model for classifying a structure or material in an image of a subject, including initializing parameters of the classification machine learning model;
(b) update the parameters of the classification machine learning model by running a learning algorithm on the training data;
(c) test the classification machine learning model on the testing set;
(d) evaluate whether the classification machine learning model has satisfactory performance;
repeat steps (a) to (d) when the performance is found in step (d) not to be satisfactory; and
output the classification machine learning model for deployment as a trained classification machine learning model, or flag the classification machine learning model as a trained classification machine learning model;
wherein each of the training and testing sets includes at least one of the annotated segmentation maps of the image and at least some annotated non-image data; and
each of the annotated segmentation maps corresponding to a respective image represents the image.

13. A system as claimed in claim 12, further comprising a segmenter configured to perform said segmenting of the one or more images, the segmenter comprising:
i) a structure segmenter configured to generate structure segmentation maps of the respective image including categorizations of the pixels or voxels assigned from a predefined set of structure categories, ii) a material segmenter configured to generate material segmentation maps of the respective image including categorizations of the pixels or voxels assigned from a predefined set of material categories, iii) a structure segmenter configured to generate structure segmentation maps of the respective image including categorizations of the pixels or voxels assigned from a predefined set of structure categories with a structure segmentation machine learning model, and/or iv) a material segmenter configured to generate material segmentation maps of the respective image including categorizations of the pixels or voxels assigned from a predefined set of material categories with a material segmentation machine learning model.

14. A system as claimed in claim 12, further comprising a segmentation map processor configured to down-sample or otherwise process the segmentation maps.

15. A system as claimed in claim 12, further comprising a segmenter configured to perform said segmenting of the one or more images, the segmenter comprising:

an abnormality segmenter configured to generate abnormality segmentation maps of the respective image including categorizations of the pixels or voxels assigned from a predefined set of abnormality or normality categories, or an abnormality segmenter configured to generate abnormality segmentation maps of the respective image including categorizations of the pixels or voxels assigned from a predefined set of abnormality or normality categories with an abnormality segmentation model.

16. A system as claimed in claim 12, further comprising a segmenter configured to perform said segmenting of the one or more images, the segmenter comprising:

i) a structure segmenter configured to generate structure segmentation maps of the respective image including categorizations of the pixels or voxels assigned from a predefined set of structure categories, and a material segmenter configured to generate material segmentation maps of the respective image including categorizations of the pixels or voxels assigned from a predefined set of material categories; or ii) a structure segmenter configured to generate structure segmentation maps of the respective image including categorizations of the pixels or voxels assigned from a predefined set of structure categories with a structure segmentation machine learning model, and a material segmenter configured to generate material segmentation maps of the respective image including categorizations of the pixels or voxels assigned from a predefined set of material categories with a material segmentation machine learning model.

* * * * *